(12) United States Patent
Stewart et al.

(10) Patent No.: US 8,025,858 B2
(45) Date of Patent: Sep. 27, 2011

(54) APPARATUS AND PROCESS FOR LIGHT OLEFIN RECOVERY

(75) Inventors: Douglas G. Stewart, Wheeling, IL (US); Joseph E. Zimmermann, Arlington Heights, IL (US); Angelo P. Furfaro, Arlington Heights, IL (US); Bipin V. Vora, Naperville, IL (US)

(73) Assignee: UOP LLC, Des Plaines, IL (US)

( * ) Notice: Subject to any disclaimer, the term of this patent is extended or adjusted under 35 U.S.C. 154(b) by 341 days.

(21) Appl. No.: 11/828,433

(22) Filed: Jul. 26, 2007

(65) Prior Publication Data

US 2007/0264176 A1    Nov. 15, 2007

Related U.S. Application Data

(62) Division of application No. 10/882,531, filed on Jun. 30, 2004, now Pat. No. 7,268,265.

(51) Int. Cl.
*B01J 8/04*    (2006.01)
*C07C 1/00*    (2006.01)
*C10B 57/02*    (2006.01)

(52) U.S. Cl. ........ 422/631; 422/630; 422/634; 422/198; 422/211; 585/324; 585/259; 585/271; 208/49; 208/106

(58) Field of Classification Search .................. 422/189, 422/190, 198, 211, 630, 631, 634; 585/324, 585/259, 271; 208/49, 106
See application file for complete search history.

(56) References Cited

U.S. PATENT DOCUMENTS

| | | | |
|---|---|---|---|
| 3,928,483 A | 12/1975 | Chang et al. | 260/668 R |
| 4,025,575 A | 5/1977 | Chang et al. | 260/682 |
| 4,447,669 A | 5/1984 | Hamon et al. | 585/640 |
| 4,496,786 A | 1/1985 | Santilli et al. | 585/640 |
| 4,499,314 A | 2/1985 | Seddon et al. | 585/408 |
| 4,547,616 A | 10/1985 | Avidan et al. | 585/640 |
| 4,677,242 A | 6/1987 | Kaiser | 585/638 |
| 4,677,243 A | 6/1987 | Kaiser | 585/638 |
| 4,695,560 A | 9/1987 | Gattuso et al. | 502/222 |
| 4,843,183 A | 6/1989 | Inui | 585/640 |
| 4,861,938 A | 8/1989 | Lewis et al. | 585/640 |
| 4,973,792 A | 11/1990 | Lewis et al. | 585/638 |
| 5,095,163 A | 3/1992 | Barger | 585/640 |
| 5,126,308 A | 6/1992 | Barger et al. | 502/214 |
| 5,191,141 A | 3/1993 | Barger et al. | 585/640 |
| 5,914,433 A | 6/1999 | Marker | 585/313 |
| 6,049,017 A * | 4/2000 | Vora et al. | 585/324 |
| 6,303,839 B1 * | 10/2001 | Marker | 585/313 |
| 6,486,369 B1 | 11/2002 | Voight et al. | 585/259 |
| 2004/0254414 A1 * | 12/2004 | Hildreth et al. | 585/648 |

FOREIGN PATENT DOCUMENTS

WO   WO 2004/009519 A1   1/2004

* cited by examiner

*Primary Examiner* — Walter Griffin
*Assistant Examiner* — Lessanework Seifu
(74) *Attorney, Agent, or Firm* — Arthur E Gooding

(57) ABSTRACT

The present invention relates to a process and apparatus for the production of light olefins comprising olefins having from 2 to 3 carbon atoms per molecule from a feedstock containing heavier olefins. An intermediate cut from a fractionation column is used as olefinic feed to an olefin cracking process preferably after undergoing selective hydrogenation of diolefins. In one embodiment, a liquid side draw from a fractionation column is selectively hydrogenated and then returned to the fractionation column from which a vapor side draw containing olefins is cracked in the olefin cracking reactor.

5 Claims, 2 Drawing Sheets

APPARATUS AND PROCESS FOR LIGHT OLEFIN RECOVERY

CROSS-REFERENCE TO RELATED APPLICATION

This application is a Division of copending application Ser. No. 10/882,531 filed Jun. 30, 2004, the contents of which are hereby incorporated by reference in its entirety.

FIELD OF THE INVENTION

This invention relates to an apparatus and process for the recovery of light olefins produced by cracking heavier olefins. This invention more particularly refers to taking an intermediate cut from fractionation column as feed to an olefin cracking reactor.

BACKGROUND OF THE INVENTION

Light olefins, ethylene and propylene, serve as feeds for plastics production and for the production of petrochemicals which serve as feeds for plastics production. The demand for light olefins has been steadily increasing and will continue to increase dramatically. Light olefins have traditionally been produced through the process of steam or catalytic cracking. Paraffin dehydrogenation is an alternative source of light olefins. However, the demand for light olefins is outstripping the capacity of traditional sources of light olefins.

The search for alternative materials for light olefin production has led to the use of oxygenates such as alcohols and, more particularly, to the use of methanol, ethanol and higher alcohols or their derivatives. These alcohols may be produced by fermentation or from synthesis gas. Synthesis gas can be produced from natural gas, petroleum liquids and from carbonaceous materials including coal, recycled plastics, municipal wastes, or any organic material. Thus, alcohol and alcohol derivatives may provide non-petroleum based routes for the production of olefins and other hydrocarbons. Methanol, in particular, is useful in this process which is referred to herein as the methanol-to-olefin (MTO) process.

Molecular sieve catalysts such as the microporous crystalline zeolite and non-zeolitic catalysts, particularly silicoaluminophosphates (SAPO), are known to promote the conversion of oxygenates to hydrocarbon mixtures. Numerous patents describe this process for various types of these catalysts: U.S. Pat. No. 3,928,483; U.S. Pat. No. 4,025,575; U.S. Pat. No. 4,252,479; U.S. Pat. No. 4,496,786; U.S. Pat. No. 4,547,616; U.S. Pat. No. 4,677,243; U.S. Pat. No. 4,843,183; U.S. Pat. No. 4,499,314; U.S. Pat. No. 4,447,669; U.S. Pat. No. 5,095,163; U.S. Pat. No. 5,191,141; U.S. Pat. No. 5,126,308; U.S. Pat. No. 4,973,792; and U.S. Pat. No. 4,861,938.

The MTO process may be generally conducted in the presence of one or more diluents which may be present in the oxygenate-containing feed in an amount between about 1 and about 99 mol-%, based on the total number of moles of all feed and diluent components fed to the reaction zone. Diluents include, but are not limited to, helium, argon, nitrogen, carbon monoxide, carbon dioxide, hydrogen, water, paraffins, hydrocarbons (such as methane and the like), aromatic compounds, or mixtures thereof. U.S. Pat. No. 4,861,938 and U.S. Pat. No. 4,677,242 particularly emphasize the use of a diluent combined with the feed to the reaction zone to maintain sufficient catalyst selectivity toward the production of light olefin products, particularly ethylene.

Generally, the product ratio of ethylene to propylene on a carbon basis varies from about 0.1 to about 10 and, more typically, varies from about 0.8 to about 2.5. Ethylene and propylene are particularly desirable olefins but it has been found that their yields are reduced by the production of medium-weight hydrocarbons such as $C_4$ to $C_8$ olefins, as well as some heavier components. U.S. Pat. No. 5,914,433 proposes cracking medium-weight olefins over a catalyst in vapor phase to increase overall yield of light olefins.

A portion of the medium-weight olefin stream, when cracked, will be converted to paraffinic compounds such as methane, ethane, propane, and heavier hydrocarbons. Unless at least a portion of these compounds are removed, they will build up in the system and reduce the overall efficiency of the process. Therefore, a drag stream comprising $C_4$ and heavier hydrocarbons is removed from the process and used for plant fuel, blended into other hydrocarbon products such as motor gasoline or used as feed to a gasoline alkylation process.

In order to maximize the production of light olefins and to minimize the production of methane produced from cracking the medium-weight olefin stream, diolefins and acetylenes should be minimized in the feed to the olefin cracking zone. Diolefin and acetylene conversion to monoolefin hydrocarbons may be accomplished with a conventional selective hydrogenation process such as disclosed in U.S. Pat. No. 4,695,560.

In a light olefins recovery flow scheme, U.S. Pat. No. 6,486,369 discloses a single selective hydrogenation converter for treating methyl acetylene and propadiene in a feed to a deethanizer column. WO 2004/009519 A1 discloses a fractionation scheme for recovering light olefins from a medium-weight olefin containing stream.

SUMMARY OF THE INVENTION

In the present invention, an intermediate cut is taken from a product fractionation column and delivered to the olefin cracking reactor. Additionally, the intermediate cut can be taken below a tray to withdraw a vapor stream from the fractionation column for feed to the olefin cracking reactor thereby obviating the need to vaporize the feed to the olefin cracking reactor. Moreover, liquid olefinic feed is mixed with a liquid side cut taken from a fractionation tray and hydrogen and selectively hydrogenated in a reactor to reduce concentrations of diolefins and acetylenes. Hydrogenated feed returned to a lower section of the column ascends in the column until withdrawn as vapor to be cracked in the olefin cracking reactor. A $C_3$ and lighter product stream is withdrawn from the overhead of the fractionation column.

An object of the present invention is to simplify the recovery section of an olefin cracking process by incorporating an intermediate cut of a fractionation column as feed to the olefin cracking reactor.

DETAILED DESCRIPTION OF THE INVENTION

Figure 1:
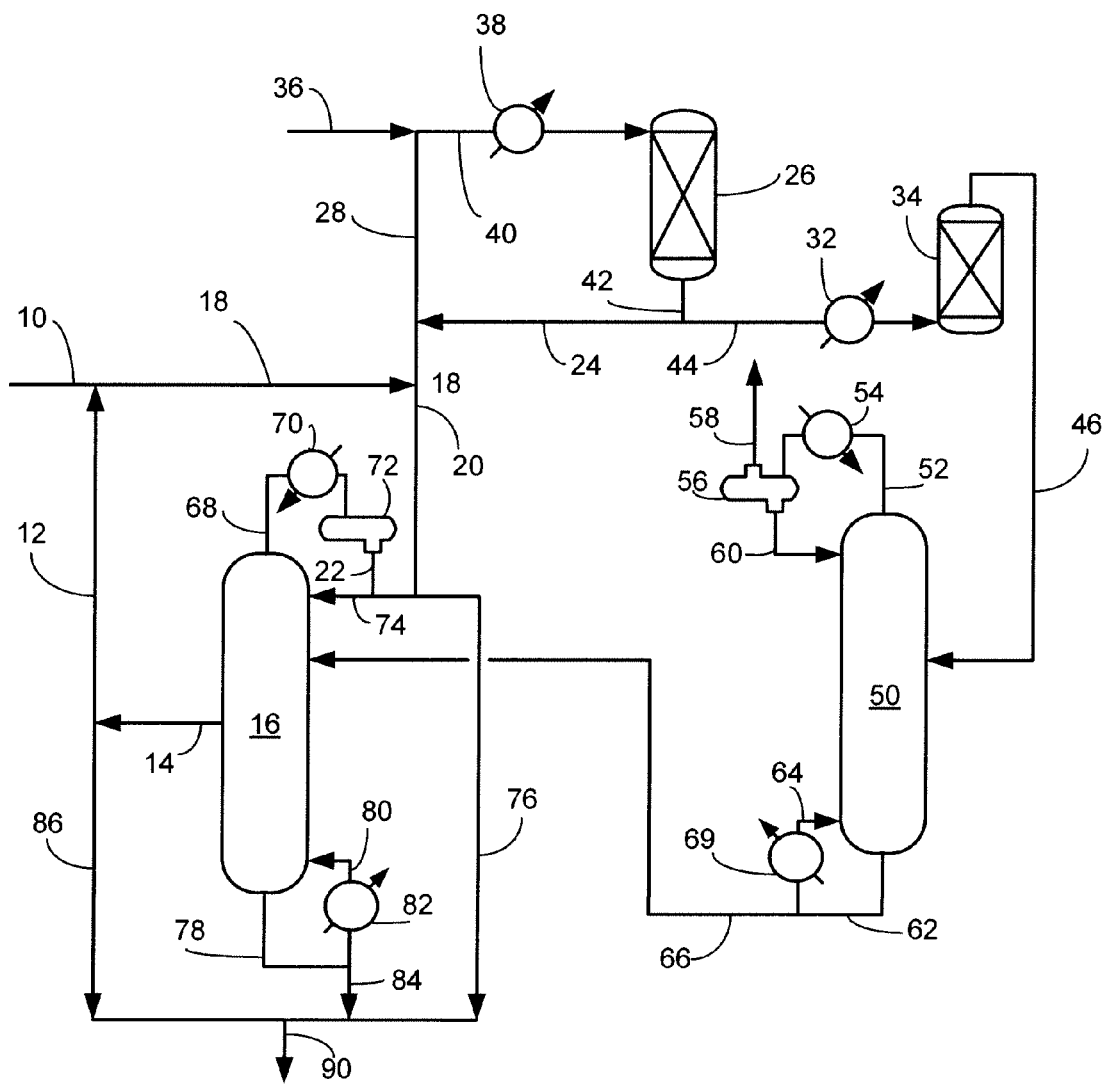
FIG. 1 is a schematic process flow diagram illustrating the process and apparatus of the present invention.

The invention comprises a process and apparatus for the catalytic conversion of an olefinic feed stream containing intermediate-weight $C_4$ to $C_7$ olefins to a cracked product stream containing light olefins, $C_2$ to $C_3$ olefins. The olefinic feed stream may be obtained from a mid-cut, $C_4$ to $C_8$ range, of a fluid catalytic cracking (FCC) product stream or from a $C_4$ to $C_6$ stream of a steam cracker furnace which contain abundant olefinic species in the desired intermediate weight range. Moreover, a $C_4^+$ product from an MTO unit, which converts oxygenates over a silicoaluminophosphate molecular sieve catalyst to light olefins as described in U.S. Pat. No. 5,914,433, would also serve well for upgrading overall process selectivity to light olefins. Increased yield of the light-weight olefinic products for all of the processes is provided by sending $C_4$ to $C_8$ medium-weight olefins to an olefin cracking reactor. Depending upon operating conditions, the medium-weight olefins may be $C_4$ to $C_5$-$C_7$ olefins.

Catalysts suitable for olefin cracking comprise a crystalline silicate of the MFI family which may be a zeolite, a silicalite or any other silicate in that family or the MEL family which may be a zeolite or any other silicate in that family. Examples of MFI silicates are ZSM-5 and Silicalite. An example of an MEL zeolite is ZSM-11 which is known in the art. Other examples are Boralite D and silicalite-2 as described by the International Zeolite Association (ATLAS OF ZEOLITE STRUCTURE TYPES, 1987, Butterworths). The preferred crystalline silicates have pores or channels defined by ten oxygen rings and a high silicon/aluminum atomic ratio.

The crystalline silicate catalyst has structural and chemical properties and is employed under particular reaction conditions whereby the catalytic cracking of the $C_4$ to $C_7$ olefins readily proceeds. Different reaction pathways can occur on the catalyst. Suitable olefin cracking process conditions include an inlet temperature of around 400° to 600° C., preferably from 520° to 600° C., yet more preferably 540° to 580° C., and an olefin partial pressure of from 10 to 202 kPa absolute (1.5 to 29 psia), preferably from 50 to 152 kPa absolute (7 to 22 psia). Furthermore, such isomerization tends to reach a thermodynamic equilibrium. Olefinic catalytic cracking may be understood to comprise a process yielding shorter molecules via bond breakage.

A crystalline silicate catalyst possessing a high silicon/aluminum ratio can achieve a stable olefin conversion with a high propylene yield on an olefin basis of from 20 to 50 wt-% with the olefinic feedstocks of the present invention. The MFI catalyst having a high silicon/aluminum atomic ratio for use in the catalytic olefin cracking process of the present invention may be manufactured by removing aluminum from a commercially available crystalline silicate. A typical commercially available Silicalite has a silicon/aluminum atomic ratio of around 120. The commercially available MFI crystalline silicate may be modified by a steaming process which reduces the tetrahedral aluminum in the crystalline silicate framework and converts the aluminum atoms into octahedral aluminum in the form of amorphous alumina. Although in the steaming step aluminum atoms are chemically removed from the crystalline silicate framework structure to form alumina particles, those particles cause partial obstruction of the pores or channels in the framework. This inhibits the olefin cracking process. Accordingly, following the steaming step, the crystalline silicate is subjected to an extraction step wherein amorphous alumina is removed from the pores and the micropore volume is, at least partially, recovered. The physical removal, by a leaching step, of the amorphous alumina from the pores by the formation of a water-soluble aluminum complex yields the overall effect of de-alumination of the MFI crystalline silicate. In this way by removing aluminum from the MFI crystalline silicate framework and then removing alumina formed therefrom from the pores, the process aims at achieving a substantially homogeneous de-alumination throughout the whole pore surfaces of the catalyst. This reduces the acidity of the catalyst and thereby reduces the occurrence of hydrogen transfer reactions in the cracking process. The reduction of acidity ideally occurs substantially homogeneously throughout the pores defined in the crystalline silicate framework. This is because in the olefin-cracking process hydrocarbon species can enter deeply into the pores. Accordingly, the reduction of acidity and thus the reduction in hydrogen transfer reactions which would reduce the stability of the MFI catalyst are pursued throughout the whole pore structure in the framework. The framework silicon/aluminum ratio may be increased by this process to a value of at least about 180, preferably from about 180 to 1000, more preferably at least 200, yet more preferably at least 300 and most preferably around 480.

The MEL or MFI crystalline silicate catalyst may be mixed with a binder, preferably an inorganic binder, and shaped to a desired shape, e.g. extruded pellets. The binder is selected so as to be resistant to the temperature and other conditions employed in the catalyst manufacturing process and in the subsequent catalytic cracking process for the olefins. The binder is an inorganic material selected from clays, silica, metal oxides such as $ZrO_2$ and/or metals, or gels including mixtures of silica and metal oxides. The binder is preferably alumina-free, although aluminum in certain chemical compounds as in $AlPO_4$ may be used as the latter are quite inert and not acidic in nature. If the binder which is used in conjunction with the crystalline silicate is itself catalytically active, this may alter the conversion and/or the selectivity of the catalyst. Inactive materials for the binder may suitably serve as diluents to control the amount of conversion, so that products can be obtained economically and orderly without employing other means for controlling the reaction rate. It is desirable to provide a catalyst having a good crush strength to prevent the catalyst from breaking down into powder-like materials during use. Such clay or oxide binders have been employed normally for the purpose of improving the crush strength of the catalyst. A particularly preferred binder for the catalyst of the present invention comprises silica or $AlPO_4$.

The relative proportions of the finely divided crystalline silicate material and the inorganic oxide matrix of the binder can vary widely. Typically, the binder content ranges from 5 to 95% by weight, more typically from 20 to 50% by weight, based on the weight of the composite catalyst. Such a mixture of crystalline silicate and an inorganic oxide binder is referred to as a formulated crystalline silicate.

In mixing the catalyst with a binder, the catalyst may be formulated into pellets, spheres, extruded into other shapes, or formed into a spray-dried powder. In the catalytic cracking process, the process conditions are selected in order to provide high selectivity towards propylene or ethylene, as desired, a stable olefin conversion over time, and a stable olefinic product distribution in the effluent. Such objectives are favored by the use of a low acid density in the catalyst (i.e. a high Si/Al atomic ratio) in conjunction with a low pressure, a high inlet temperature and a short contact time, all of which process parameters are interrelated and provide an overall cumulative effect.

The process conditions are selected to disfavor hydrogen transfer reactions leading to the formation of paraffins, aromatics and coke precursors. The process operating conditions thus employ a high space velocity, a low pressure and a high reaction temperature. The LHSV ranges from 5 to 30 $hr^{-1}$, preferably from 10 to 30 $hr^{-1}$. The olefin partial pressure ranges from 10 to 202 kPa absolute (1.5 to 29 psia), preferably from 50 to 152 kPa absolute (7 to 22 psia). A particularly preferred olefin partial pressure is atmospheric pressure. The hydrocarbon feedstocks are preferably fed at a total inlet pressure sufficient to convey the feedstocks through the reactor. The hydrocarbon feedstocks may be fed undiluted or diluted in an inert gas, e.g. nitrogen or steam. The total absolute pressure in the reactor ranges from 30 to 1013 kPa absolute (4 to 147 psia) and is preferably atmospheric. The use of a low olefin partial pressure, for example atmospheric pressure, tends to lower the incidence of hydrogen transfer reactions in the cracking process, which in turn reduces the potential for coke formation which tends to reduce catalyst stability. The cracking of the olefins is preferably performed at an inlet temperature of the feedstock of from 400° to 650° C., more preferably from 450° to 600° C., yet more preferably from 540° to 590° C., typically around 560° to 585° C.

In order to maximize the amount of ethylene and propylene and to minimize the production of methane produced from the butylene and heavier stream, it is desired to minimize the presence of diolefins and acetylenes in the feed. Diolefin conversion to monoolefin hydrocarbons may be accomplished with a conventional selective hydrogenation catalyst which comprises an alumina support material preferably having a total surface area greater than 150 m$^2$/g, with most of the total pore volume of the catalyst provided by pores with average diameters of greater than 600 angstroms, and containing surface deposits of about 1.0 to 25.0 wt-% nickel and about 0.1 to 1.0 wt. % sulfur such as disclosed in U.S. Pat. No. 4,695,560. Spheres having a diameter between about 0.4 and 6.4 mm (¹⁄₆₄ and ¼ inch) can be made by oil dropping a gelled alumina sol. The alumina sol may be formed by digesting aluminum metal with an aqueous solution of approximately 12 wt-% hydrogen chloride to produce an aluminum chloride sol. The nickel component may be added to the catalyst during the sphere formation or by immersing calcined alumina spheres in a aqueous solution of a nickel compound followed by drying, calcining, purging and reducing. The nickel containing alumina spheres may then be sulfided.

The selective hydrogenation processes is normally performed at relatively mild hydrogenation conditions. These conditions will normally result in the hydrocarbons being present as liquid phase materials. The reactants will normally be maintained under the minimum pressure sufficient to maintain the reactants as liquid phase hydrocarbons which allows the hydrogen to dissolve into the hydrocarbonaceous hydrogenation feed. A broad range of suitable operating pressures therefore extends from about 276 to 5516 kPa gauge (40 to about 800 psig), with a pressure between about 345 and 2069 kPa gauge (50 and 300 psig) being preferred. A relatively moderate temperature between about 25° C. and about 350° C. (77° to 662° F.) should be employed. Preferably, the temperature of the hydrogenation zone is maintained between about 30° and about 200° C. (122° and 392° F.). The liquid hourly space velocity of the reactants through the selective hydrogenation catalyst should be above 1.0 hr$^{-1}$. Preferably, it is above 5.0 and more preferably it is between 5.0 and 35.0 hr$^{-1}$. The ratio of hydrogen to diolefinic hydrocarbons maintained within the selective hydrogenation zone is an important variable. The amount of hydrogen required to achieve a certain conversion is believed dependent upon both reactor temperature and the molecular weight of the feed hydrocarbons. To avoid the undesired saturation of a significant amount monoolefinic hydrocarbons, there should be less than 2.0 times the stoichiometric amount of hydrogen required for the selective hydrogenation of the diolefinic hydrocarbons which are present in the liquid phase process stream to monoolefinic hydrocarbons. Preferably, the mole ratio of hydrogen to diolefinic hydrocarbons in the material entering the bed of selective hydrogenation catalyst is maintained between 1:1 and 1.8:1. In some instances, it may be desirable to operate with a less than stoichiometrically required amount of hydrogen, with mole ratios down to 0.75:1 being acceptable. The optimum set of conditions will of course vary depending on such factors as the composition of the feed stream and the degree of saturation of diolefinic hydrocarbons which is desired.

The hydrogenation reactor is preferably a cylindrical fixed bed of catalyst through which the reactants move in a vertical direction. It is preferred that the reactants flow upward through the reactor as this provides good mixing. The hydrogenation catalyst may be present within the reactor as pellets, spheres, extrudates, irregular shaped granules, etc. To employ the hydrogenation catalyst, the reactants would be preferably brought to the desired inlet temperature of the reaction zone, admixed with hydrogen and then passed into and through the reactor. Alternatively, the reactants may be admixed with the desired amount of hydrogen and then heated to the desired inlet temperature. In either case, the effluent of the hydrogenation reactor may be passed into a hydrogen recovery facility for the removal of residual hydrogen before proceeding further in the process. Hydrogen may be removed by flashing the hydrogenation effluent stream to a lower pressure or by passing the effluent stream into a stripping column. Otherwise, no residual hydrogen recovery may be necessary if the residual hydrogen concentration in the hydrogenation effluent is acceptable. The effluent from the selective hydrogenation reactor will preferably have less than 100 ppm of diolefins. The selective hydrogenation reactor may be omitted if the concentration of diolefins is already below 100 ppm.

A portion of the olefin cracking feed, when cracked, will be converted to paraffinic compounds such as methane, ethane, propane, and heavier hydrocarbons. Hydrogenation may have the same effect. Unless at least a portion of these paraffinic compounds is removed, they will build up in the system. Therefore, a drag stream comprising $C_4$ and heavier hydrocarbons is removed from the process and used for plant fuel or blended into other hydrocarbon products such as motor gasoline. Additionally, paraffins can be returned to the FCC unit or to the steam cracker for further cracking.

A depropanizer fractionation column may be used for light olefin recovery in the overhead. Further downstream processing may be necessary to separate paraffins from olefins and to separately recover propylene and ethylene. The depropanizer column may be run at a pressure of 800 to 2100 kPa absolute (116 to 305 psia). Hence, a compressor may be required to pressurize the cracked olefin effluent before entering the depropanizer. A debutanizer fractionation column may used to collect and redirect a portion of the depropanizer bottoms stream for process recycle. The debutanizer column may be run at pressure similar to the depropanizer column but is typically less.

DETAILED DESCRIPTION OF THE DRAWINGS

The following description of the present process is made with reference to the drawing. In the interest of simplifying the description of the invention, the process system in the drawing does not contain the several conduits, valves, heat exchangers, and the like which, in actual practice, would be provided in accordance with routine skill in the art to enable the process to be carried out on a continuous basis.

FIG. 1 illustrates a first embodiment of the present invention which utilizes two fractionation columns. A fresh olefinic feed comprising 20 to 50 wt-% intermediate-weight $C_4$ to $C_8$ hydrocarbons with olefins enters the process in a line 10. A line 12 carrying a liquid process side cut containing intermediate-weight $C_5$ to $C_7$ hydrocarbons with olefins from a debutanizer column 16 mixes with the line 10 to provide an enriched feed in a line 18. The enriched feed in the line 18 mixes with a process portion in a line 20 of a $C_4^-$ stream in a line 22 from the overhead of the debutanizer column 16 and then mixes with recycled hydrogenation effluent in a line 24 from a hydrogenation reactor 26 to provide an olefin hydrogenation feed in a line 28. The olefin hydrogenation feed includes diolefins and acetylenes which would convert to coke in a heater 32 preceding an olefin cracking reactor 34 and can crack to methane in the olefin cracking reactor 34. Hence, the olefin hydrogenation feed in the line 28 is admixed with hydrogen from a line 36 and heated in a heat exchanger 38 before the hydrogen containing olefin hydrogenation feed in a line 40 enters the selective hydrogenation reactor 26. The olefin hydrogenation feed is in liquid phase and the hydrogen is dissolved into the liquid hydrocarbonaceous hydrogenation feed. The liquid olefin hydrogenation feed enters the selective hydrogenation reactor 26 and contacts a preferably fixed bed of hydrogenation catalyst. The hydrogenation reactor 26 may be configured for up flow or radial flow, even though down flow is shown in FIG. 1. Under selective hydrogenation conditions, diolefins and acetylenes in the olefin hydrogenation feed are converted to monoolefins without substantial monoolefin saturation. Hydrogenation effluent with a smaller concentration of diolefins than in the olefin hydrogenation feed in the line 40 exits the hydrogenation reactor 26 in a line 42 and is split between the hydrogenation effluent recycle in the line 24 and olefin cracking feed in a line 44. The olefin cracking feed in the line 44 is heated sufficiently to enter the vapor phase in the heater 32 and gaseous olefin cracking feed enters the olefin cracking reactor 34. The heater 32 may comprise several stages of heating including a heat exchange with effluent from the olefin cracking reactor 34. In the olefin cracking reactor 34, the olefin cracking feed contacts olefin cracking catalyst under gaseous phase conditions. Although the olefin cracking reactor 34 is shown to be an upflow reactor, it may be oriented to be in a down flow or radial flow configuration. Upon contacting the olefin cracking catalyst under olefin cracking conditions, heavy olefins in the $C_4$ to $C_7$ range crack down to light olefins in the $C_2$ to $C_3$ range. Cracked olefin effluent leaves the olefin cracking reactor 34 in a line 46 and feeds a depropanizer column 50. An overhead $C_3^-$ stream comprising light olefins in a overhead line 52 is cooled in a condenser 54 and split in a receiver 56 between a $C_3^-$ product stream 58 and a reflux stream 60. A bottoms stream in a line 62 is split between a reboil line 64 and a debutanizer feed line 66. The reboil line 64 is heated in a reboiler 69 and returned to the depropanizer column 50 while the debutanizer feed line 66 is fed to the debutanizer column 16. A debutanizer overhead line 68 carrying a $C_4^-$ stream with olefins is condensed in a condenser 70 and enters a receiver 72. The effluent from the receiver 72 in the line 22 is split between a debutanized process stream in the line 20, a purge stream in a line 76 and a reflux stream in a line 74. The bottoms stream in a line 78 comprising $C_8$ hydrocarbons is split between a reboil stream 80 which is reboiled in a reboiler 82 and returned to the debutanizer column 16 and a bottom purge portion in a line 84. An intermediate cut of $C_5$ to $C_7$ hydrocarbons with olefins in a line 14 from a side draw in the debutanizer column 16 is split between a process side cut in the line 12 and a purge side cut in a line 86. The purges in the lines 76, 84 and 86 are all combined in a stream 90 to be mixed in a motor fuel pool or recycled upstream to a unit which provided fresh olefinic feed in the line 10. The purge provides for the elimination of $C_4^+$ paraffins which would otherwise build up in the process.

Figure 2:
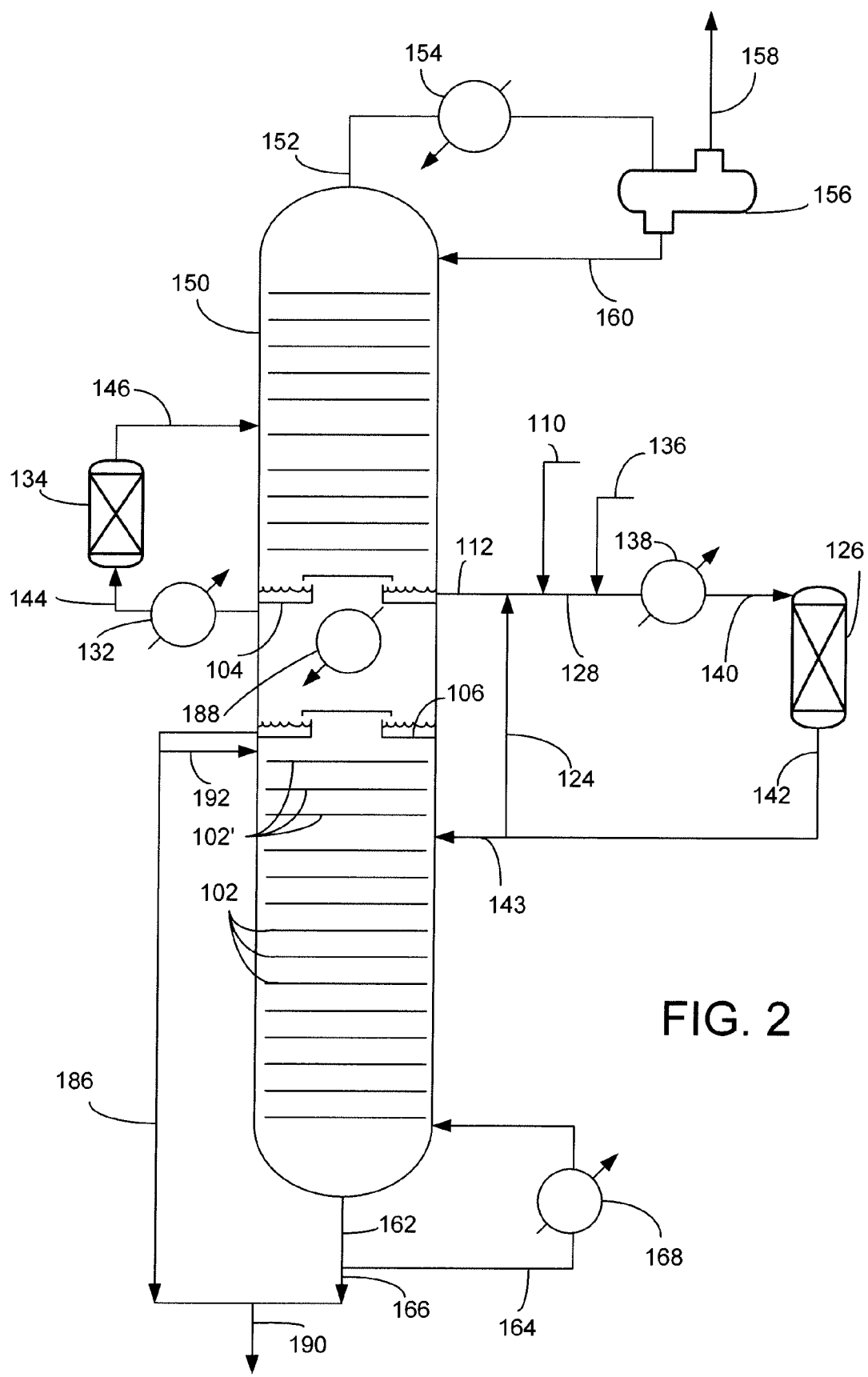
FIG. 2 is a schematic process flow diagram illustrating an alternative process and apparatus of the present invention.

FIG. 2 depicts an alternative embodiment of the present invention that omits the need for one of the fractionation columns, preferably the debutanizer column 16 in FIG. 1. A fresh olefinic feed comprising 20 to 50 wt-% intermediate-weight $C_4$ to $C_8$ hydrocarbons with olefins enters the process in a line 110. A line 112 carrying an intermediate cut containing intermediate-weight $C_5$ to $C_7$ hydrocarbons with olefins from a depropanizer column 150 mixes with a recycled hydrogenated effluent in a line 124 before mixing with the fresh olefinic feed in the line 110 to provide an olefin hydrogenation feed in a line 128. The depropanizer fractionation column 150 includes several trays 102, but a tray 104 is a total liquid accumulator that includes a liquid trap for collecting liquid and from which the line 112 takes a side draw, so that the intermediate cut in the line 112 is substantially all liquid. The olefin hydrogenation feed includes diolefins and acetylenes which can crack to methane in an olefin cracking reactor 134. Hence, the olefin hydrogenation feed in the line 128 is admixed with hydrogen from a line 136 and temperature controlled in a heat exchanger 138 before the hydrogen containing olefin hydrogenation feed in a line 140 enters a selective hydrogenation reactor 126. The olefin hydrogenation feed is in liquid phase and the hydrogen is dissolved into the liquid hydrocarbonaceous hydrogenation feed. The liquid olefin hydrogenation feed enters the hydrogenation reactor 126 and contacts a preferably fixed bed of hydrogenation catalyst. The hydrogenation reactor 126 may be configured for up flow or radial flow, although down flow is shown in FIG. 2. Under selective hydrogenation conditions, diolefins and acetylenes in the olefin hydrogenation feed are converted to monoolefins without substantial monoolefin saturation. Hydrogenation effluent with a smaller concentration of diolefins than in the olefin hydrogenation feed in the line 128 exits the hydrogenation reactor 126 in a line 142 and is split between the hydrogenation effluent recycle in the line 124 and the depropanizer column feed in a line 143. The depropanizer column feed in the line 143 is delivered to a depropanizer column 116 at a point that is preferably below the point from which the liquid side draw is taken by the line 112. Lighter components of the hydrogenation effluent are distilled upwardly in the depropanizer column 116 and a side vapor draw is taken preferably below the tray 104 from which the liquid draw is taken and above the point at which the line 143 delivers depropanizer column feed. The side vapor draw is taken through a line 144 and comprises olefin cracking feed. The olefin cracking feed in the line 144 is heated in a heat exchanger 132 and delivered to the olefin cracking reactor 134. Hence, the line 142 carrying hydrogenated effluent fluidly communicates with the line 144 carrying olefin cracking feed through the depropanizer column 150. Because the olefin cracking feed in the line 144 is a vapor draw from the depropanizer column 150, the heat exchanger 132 does not have to provide heat of vaporization necessary to evaporate the liquid hydrogenated effluent in the line 143, thereby requiring less heat duty. In the olefin cracking reactor 134, the olefin cracking feed contacts olefin cracking catalyst under gaseous phase conditions. Although the olefin cracking reactor 134 is shown to be an upflow reactor, it may be oriented to be in a down flow or radial flow configuration. Upon contacting the olefin cracking catalyst under olefin cracking conditions, heavy olefins in the $C_4$ to $C_7$ range crack down to light olefins in the $C_2$ to $C_3$ range. Cracked olefin effluent leaves the olefin cracking reactor 134 in a line 146 which feeds the depropanizer column 150, preferably at a point that is higher than the point at which the vapor side draw is taken by the line 144 and the point at which the liquid side draw is taken by the line 112. An overhead $C_3^-$ stream comprising light olefins in an overhead line 152 is cooled in a condenser 154 and split in a receiver 156 between a $C_3^-$ product stream 158 and a reflux stream 160. A bottoms stream in a line 162 comprising $C_8^+$ hydrocarbons is split between a reboil line 164 and a purge line 166. The reboil line 164 is heated in a reboiler 168 and returned to the depropanizer column 150 while the bottoms purge is removed in the purge line 166.

Optionally, an intermediate cut of $C_5$ to $C_7$ hydrocarbons may be purged by a purge line 186 at a point below the point at which vapor and liquid side draws are taken by the lines 144 and 112, respectively, and above the point at which hydrogenation effluent feeds the depropanizer column 150 by the line 143. The liquid purge may be taken from a tray 106 by the purge line 186 and mixed with the purge line 166 in a line 190. An optional condenser 188 either stabbed in or in fluid communication with the depropanizer column 150 below the tray 104 and above the tray 106 may be used to adjust the proportion of heavy paraffins in the feed withdrawn in the line 144 and delivered to the olefin cracking reactor 134. If the condenser 188 is used, a reflux line 192 may be used to return liquid to the depropanizer column 150. Optional trays 102' are only used if the optional equipment, the tray 106, the condenser 188, the purge line 186 and the reflux line 192, are utilized. Otherwise, the depropanizer column 150 includes no trays between the tray 104 and the hydrogenation effluent inlet line 143.

The invention claimed is:

1. An apparatus for the production of light olefins comprising:
    a hydrogenation reactor containing hydrogenation catalyst for selectively hydrogenating diolefins in an olefin stream with hydrogen to obtain monoolefins, providing an olefin cracking feed;
    at least one hydrogenation effluent conduit fluidly communicating an outlet of said hydrogenation reactor with an inlet to an olefin cracking reactor;
    means for vaporizing hydrogenated effluent in fluid communication with said hydrogenation effluent conduit, wherein the means for vaporizing the hydrogenated effluent and the outlet of the hydrogenation reactor are connected through a pipe without any intervening processing units;
    the olefin cracking reactor containing olefin cracking catalyst for converting olefins in the olefin cracking feed into a cracked olefin stream comprising $C_2$ and $C_3$ olefins, and in communication with the means for vaporizing the hydrogenated effluent, wherein the olefin cracking reactor inlet and the means for vaporizing the hydrogenated effluent are connected through a pipe without any intervening processing units;
    a fractionation zone in fluid communication with said olefin cracking reactor for separating light hydrocarbons from heavy hydrocarbons in said cracked olefin stream, said fractionation zone including at least one fractionation column; and
    a side cut conduit fluidly communicating a side cut from said fractionation column to an olefin feed line for mixing with the olefin feed to said hydrogenation reactor or to said olefin cracking reactor.

2. The apparatus of claim 1 wherein the fractionation zone includes two fractionation columns and the side cut is taken from the second fractionation column and the light olefin product is taken from the first fractionation column.

3. The apparatus of claim 1 wherein the fractionation zone includes just one column.

4. The apparatus of claim 3 wherein the side cut is taken from a liquid draw tray and the side cut conduit fluidly communicates with the hydrogenation reactor.

5. The apparatus of claim 3 wherein the side cut is taken from a vapor stream and the side cut conduit fluidly communicates with said olefin cracking reactor.

* * * * *